United States Patent
Lenarz et al.

(10) Patent No.: US 6,208,882 B1
(45) Date of Patent: Mar. 27, 2001

(54) STAPEDIUS REFLEX ELECTRODE AND CONNECTOR

(75) Inventors: Thomas H. R. Lenarz, Hannover (DE); Thomas J. Balkany, Coral Gables, FL (US); Janusz A. Kuzma, Englewood, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/323,594

(22) Filed: Jun. 1, 1999

Related U.S. Application Data

(60) Provisional application No. 60/087,810, filed on Jun. 3, 1998, and provisional application No. 60/099,750, filed on Sep. 10, 1998.

(51) Int. Cl.[7] ............................................. A61B 5/04
(52) U.S. Cl. ............................................. 600/379; 607/137
(58) Field of Search .......................... 607/137, 55–57, 607/115, 116, 118; 600/379; 29/592.1, 825, 829; 128/898

(56) References Cited

U.S. PATENT DOCUMENTS

| 4,052,754 | * | 10/1977 | Homsy | 607/137 |
| 5,476,446 | * | 12/1995 | Arenburg | 604/21 |
| 5,626,629 | * | 5/1997 | Faltys et al. | 607/57 |
| 5,674,264 |   | 10/1997 | Carter et al. | 607/57 |
| 5,758,651 |   | 7/1998 | Nygard et al. | 128/741 |

FOREIGN PATENT DOCUMENTS

| 97/09863 | * | 3/1997 | (WO) | A61B/5/12 |
| 9748447  |   | 6/1997 | (WO) | |

* cited by examiner

Primary Examiner—Jeffrey R. Jastrzab
(74) Attorney, Agent, or Firm—Bryant R. Gold

(57) ABSTRACT

A stapedius electrode attaches to or is embedded within the stapedius muscle (20) at a point near where the stapedius muscle is visible as it exits a bony channel (30) within the middle ear. In one embodiment, the electrode is made from a biocompatible metal wire formed into a flat blade (102) having a sharp tip (104) and serrations (103) along one edge. An insulated lead attaches electrically and mechanically to the blade. Such attachment may be made by welding and wrapping the insulated lead at one end of the wire around the body of the electrode and protecting such weld and securing such wrappings with a coating or blob of epoxy. During implantation of the electrode, the electrode blade is inserted through a small slot made in the muscle tissue. Alternatively, the electrode may be inserted alongside the muscle tissue through an opening in the bony wall as it passes through the bony channel, with a tip of the electrode protruding from the bony channel. The protruding tip is then bent over to lie against the bony wall, and hold the electrode in place. Other embodiments of a stapedius electrode are also presented. such as the distal end (84) of a multistrand insulated wire (82) that is embedded in the stapedius muscle tissue (20) using a delivery needle (86). A tube connector (90) may be used to electrically connect a lead coming form the implanted stapedius electrode to an implant device. The tube connector (90) includes a platinum tube (92) welded at one end to a lead (91) coming from the implant device. A proximal end (83) of the lead from the electrode is crimped to the other end of the tube (92). A silicone tube or sleeve (94) is then placed over the tube and sealed at both ends.

33 Claims, 15 Drawing Sheets

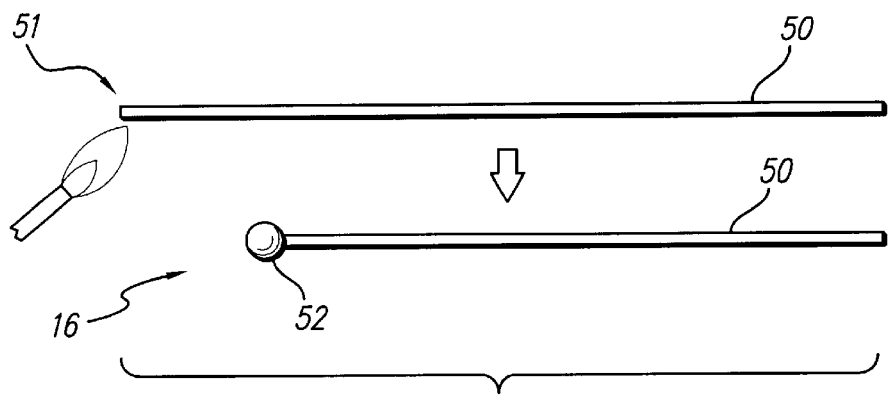
FIG. 7
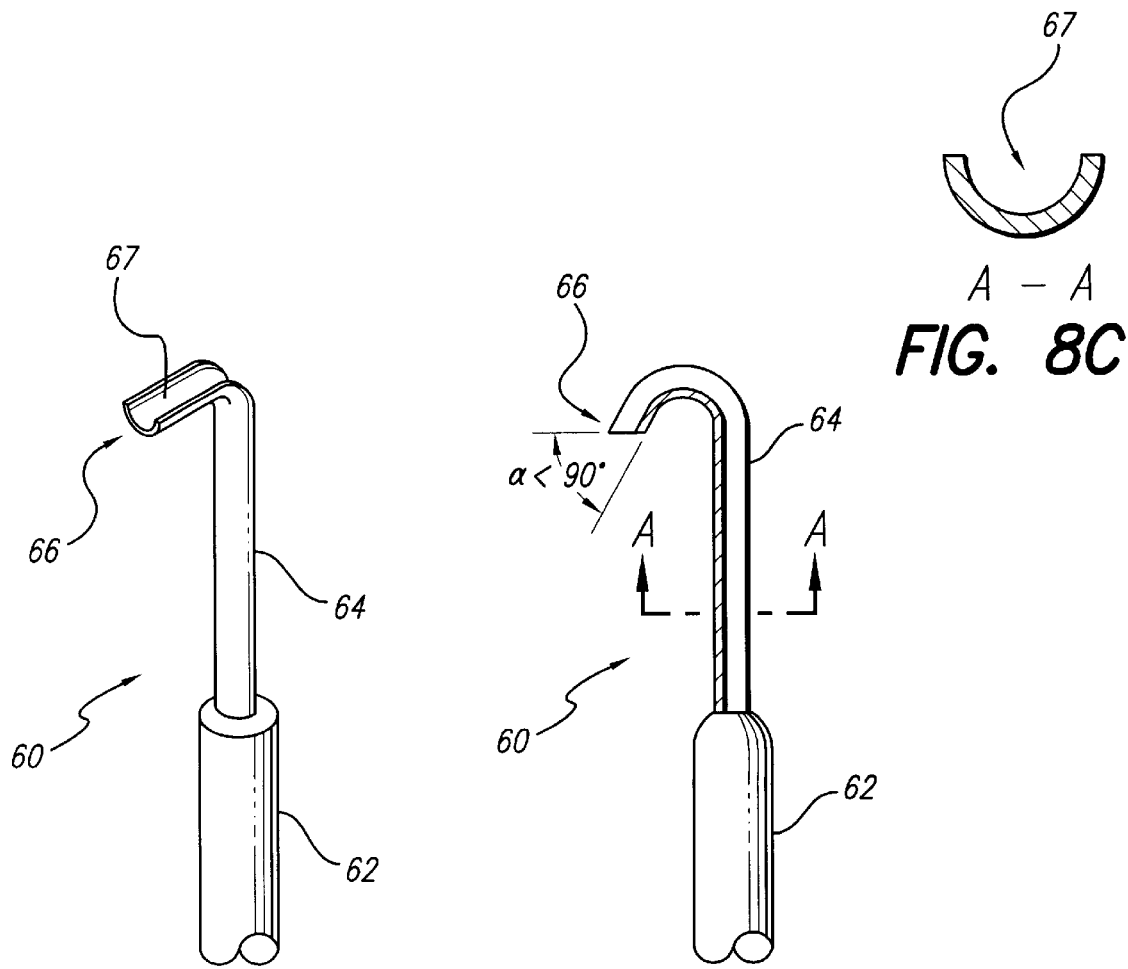
FIG. 8A  FIG. 8B  FIG. 8C

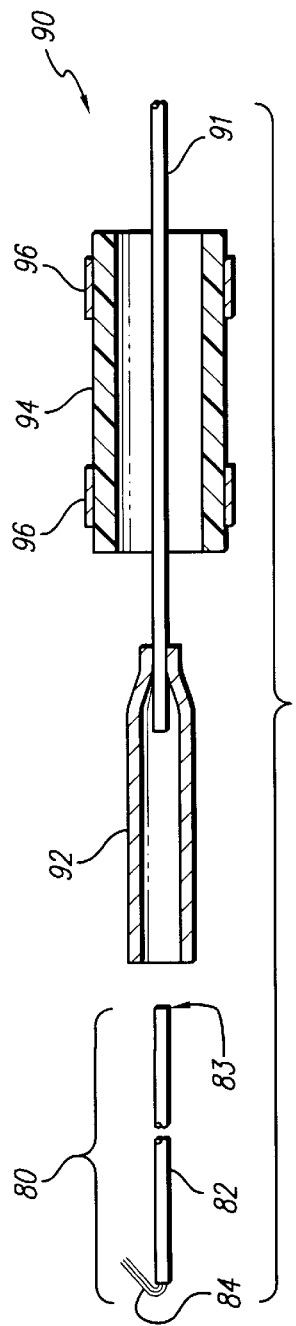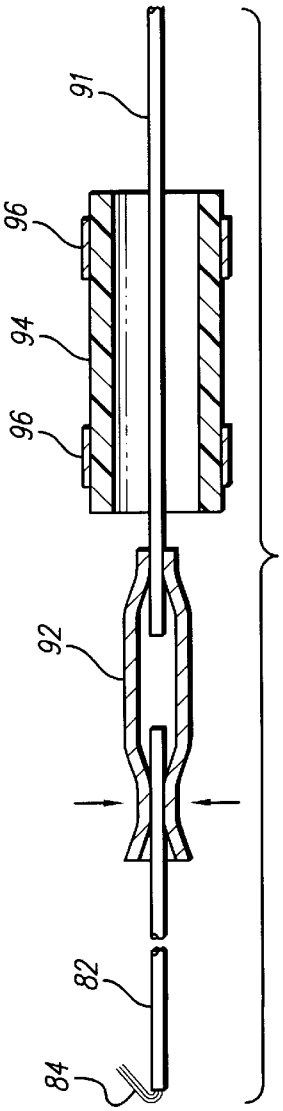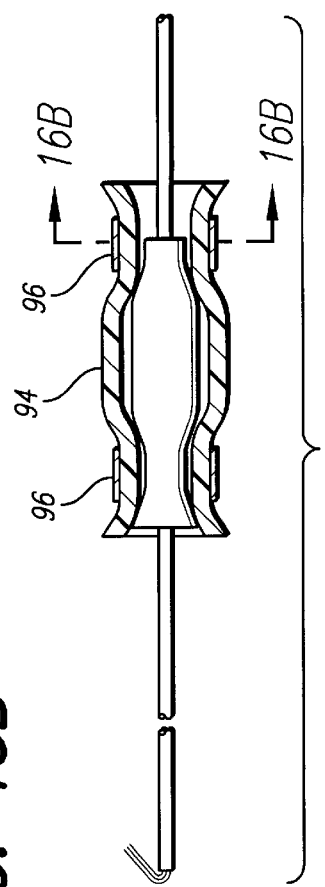

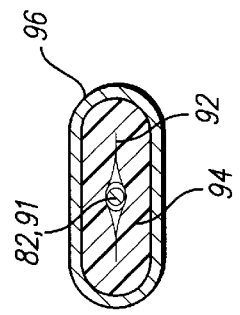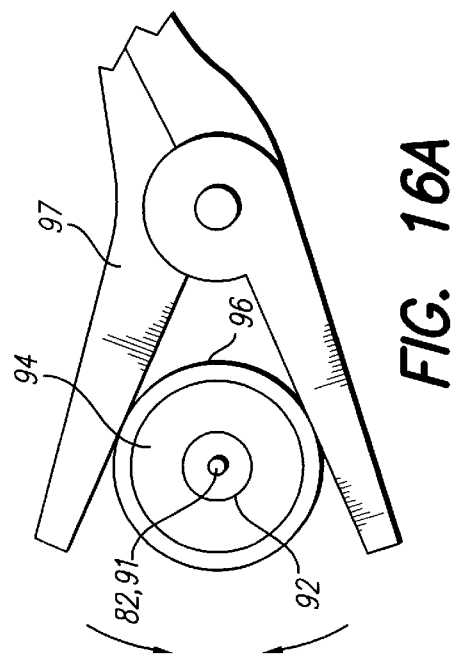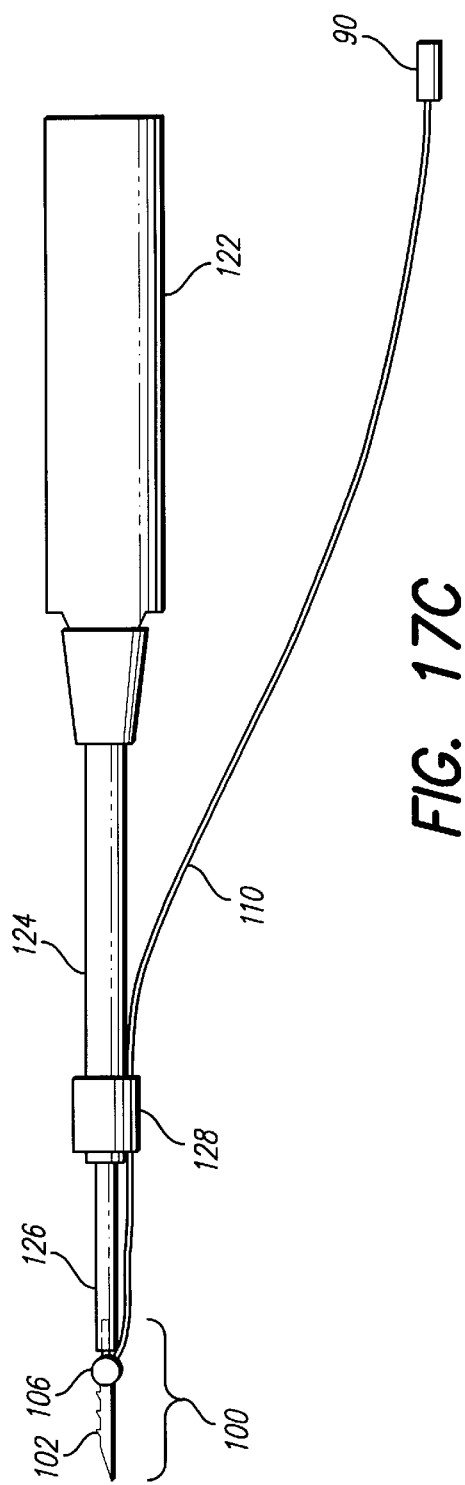
FIG. 16B
FIG. 16A
FIG. 17C

US 6,208,882 B1

STAPEDIUS REFLEX ELECTRODE AND CONNECTOR

This application claims the benefit of the following U.S. Provisional Applications Ser. No. 60/087,810, filed Jun. 3, 1998; and Ser. No. 60/099,750, filed Sep. 10, 1998.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to monitor the stapedius reflex of a patient.

In International Application Number PCT/US97/10590, filed internationally on Jun. 19, 1997, there is disclosed a self-adjusting cochlear implant system, and a method for fitting such a system, that relies, in part, on sensing the stapedius reflex of the patient. This PCT application (PCT/US97/10590) is incorporated herein by reference.

The stapedius reflex is used in cochlear implants to determine how much sound energy a patient perceives. This information is very useful in programming the cochlear implant system so that proper signal levels may be maintained. Thus, as is described in the referenced PCT application, an implantable electrode placed over or in the stapedius muscle, in conjunction with the reverse telemetry features of the implantable cochlear stimulator (ICS), which allow sensed data to be telemetered from an ICS to an external unit, provide a very useful tool to enhance the programming of the ICS.

The stapedius reflex operates in a normal ear to dampen movement of the ossicular chain, and in particular the stapes, so that excessive motion of the stapes (which could otherwise be sensed as an extremely-loud, potentially-damaging, sound) is not transmitted through the oval window into the inner ear.

Unfortunately, sensing the stapedius reflex is not an easy task. This is because the stapedius muscle, which is attached to the stapes, is hidden inside a bony channel, and only a very small part of it and its tendon are visible and/or accessible from within the middle ear. Further, because only a very small part of the muscle is accessible, it is difficult to attach an electrode to the stapedius reflex muscle without damaging the integrity of the stapedius reflex muscle.

SUMMARY OF THE INVENTION

The present invention is directed to several different electrode designs that may be used to sense the stapedius reflex of the patient without damaging the stapedius reflex muscle, to implant tools used in positioning the electrode at a desired location, and to an implantable connector that may be used to electrically connect a stapedius reflex electrode to an implantable cochlear stimulator (ICS) or other implantable unit.

A first preferred embodiment of a stapedius reflex electrode made in accordance with the present invention comprises a serrated blade electrode adapted to be inserted through a small slot made in the stapedius muscle. A suitable flexible wire, e.g., a 25 micron diameter platinum/iridium (Pt/Ir) Teflon-coated wire, is mechanically and electrically bonded to a proximal end of the blade electrode. The other end of the wire is attached to a suitable connector that eventually allows the wire to be electrically connected to appropriate monitoring circuitry. Once the blade electrode is inserted in the slot, serrations at a distal tip of the electrode, coupled with an epoxy blob resting snugly against the stapedius muscle on a proximal end of the blade electrode, hold the blade electrode securely in its desired position within the slot. The slot may be made in the stapedius muscle using a conventional needle, such as a 30G needle, or a similar sharp instrument. A special insertion tool may be used to facilitate inserting, positioning and holding of the blade electrode in its desired position within the slot made through the stapedius muscle.

A second preferred embodiment of a stapedius reflex electrode comprises a blade electrode, with or without serrations at its distal tip, that is inserted through an opening made through the bone into the bony channel through which the stapedius muscle and tendon passes. When inserted, such blade electrode lies flat against the stapedius muscle and is positioned so that its distal tip protrudes out from the bony channel pointing towards the stapes. This tip is then bent over against the outside of the bone that defines the bony channel, thereby securing the blade electrode so that it lies flat against the stapedius muscle. Such positioning of the blade electrode advantageously offers a large surface area over which stapedius reflex muscle activity may be electrically sensed.

In addition to the first and second preferred embodiments described above, the present invention also contemplates various other stapedius reflect electrodes. In a first alternative embodiment, for example, a stapedius reflex electrode comprises a biocompatible metal wire, preferably Iridium, shaped into a hook with a small ball at one end. The other end is connected to a light, coiled, insulated lead that provides a connection to the implant (monitoring) circuitry. The hook is preferably insulated, except for the surface of the ball. During implant surgery, the ball is pressed against The stapedius muscle into the bony channel.

A second alternative embodiment of a stapedius reflex electrode includes an electrical contact, made from platinum foil, embedded within a silicone mold. The silicone mold is shaped into a cuff configuration, with an opening slightly smaller than the diameter of the end of The stapedius muscle extending out of the bone. The silicone cuff has an opening allowing easy assembly of the electrode by clipping the cuff over the exposed muscle. Electrical connection of the electrode to the implant circuitry is provided by a flexible coiled, insulated lead.

A third alternative embodiment of a stapedius muscle electrode includes an electrode made from soft, annealed, platinum wire formed into a hook shape. One end is formed into a loop, or ball. The other end is connected to a coiled, insulated lead. The electrode is placed over the visible end of the stapedius muscle and crimped over the muscle to stabilize it and to provide direct contact with the muscle.

A fourth alternative embodiment of a stapedius muscle electrode comprises an electrode made from soft, annealed, platinum wire formed into a U shape. The ends of the electrode are looped, or flamed into a ball. A flexible, coiled, insulated lead is connected preferably in the middle of the U-shaped wire. The electrode is placed over The stapedius muscle and crimped to provide stability and contact.

A fifth alternative embodiment of a stapedius muscle electrode, similar to the first alternative embodiment described above, comprises a ball electrode made by flaming the distal end of a multistrand paltinum/iridium (Pt/Ir) wire. The ball electrode is adapted for implantation in a stable position, squeezed between the stapedius muscle and the bony wall. Advantageously, after a few weeks, the ball electrode partially erodes the bone at the pressure point, making a socket for itself, and thereby securing itself in a stable position. A special implant tool may be used with the ball electrode in order to insert it into its desired position between the stapedius muscle and the bony wall.

A sixth alternative embodiment of a stapedius muscle electrode comprises a harpoon electrode. The harpoon electrode is formed from multistrand Teflon-insulated Pt/Ir wire and reloaded into an insertion tool. The electrode is made at a distal end of the wire by removing about 1.0–1.5 mm of insulation. A preferred delivery tool comprises a delivery needle attached to a handle. The distal tip, with insulation removed, is left protruding from the end of the needle and is bent backwards on the needle. Implantation occurs by drilling a small hole in the bony wall near the stapedius muscle, or by removing part of the bony wall by drilling or chipping away, thereby exposing the stapedius muscle. The tip of the delivery needle is then pushed through the opening into the muscle, forcing the folded-back electrode tip into the muscle tissue. The delivery needle is then removed, which causes the folded-back end of the electrode lead to be securely fixed and embedded within the surrounding stapedius muscle tissue.

In a second approach, the electrode can also be placed at the tendon of the muscle between the bony channel and stapes.

The invention is further directed to an implantable connector that may be used with any of the above insertion techniques for a stapedius electrode. That is, the blade electrode, ball electrode or harpoon electrode described above, or other types of stapedius electrodes described herein, require the provision of a small and effective connector in order to electrically connect the wire from which the electrode is made (or connected) to appropriate monitoring circuitry, typically included within the implantable stimulator unit. Such small and effective connector may be realized by welding a small diameter platinum tubing to the distal end of the flexible lead which is connected to the stimulator. A section of silicone tubing is also placed on the lead. The silicone tubing has an internal diameter that allows it to freely slide over the platinum tubing. The silicone tubing is equipped with two platinum bands, one placed on each end of the tube. The proximal end of the lead from the electrode is placed within the opening of the platinum tube, and the tube is then squeezed with forceps to cut through the Teflon insulation so as to make good electrical contact with the multistrand wire. Then, the section of silicone tubing is placed over the platinum tube and both platinum bands are squashed or compressed, closing the openings on both ends of the silicone tube and thereby insulating the connector from body tissue and fluids.

It is an object of the invention to provide a stapedius muscle electrode that may be used within the middle ear to sense the reflex of the stapedius muscle to incoming sound energy.

It is a further object of the invention to provide a stapedius muscle electrode which provides effective signal detection without damaging the integrity of the stapedius muscle.

It is an additional object of the invention to provide a stapedius muscle electrode that is inexpensive to manufacture, easy to implant, and which can be readily connected to an implantable stimulator.

BRIEF DESCRIPTION OF THE DRAWINGS

The above and other aspects, features and advantages of the present invention will be more apparent from the following more particular description thereof, presented in conjunction with the following drawings wherein:

FIG. 7 illustrates the formation of a ball electrode at a distal end of a multistrand wire in accordance with a fifth alternative embodiment of the invention;

FIGS. 8A and 8B show a preferred implant tool that is used to implant a ball electrode of the type shown in FIG. 7;

FIG. 8C is a sectional view of the tool shown in FIGS. 8A and 8B, taken along the lines A—A in FIG. 8B;

FIGS. 15A, 15B and 15C illustrate an implantable connector made in accordance with one aspect of the invention, which connector is adapted to connect the proximal end of a lead connected to a stapedius electrode with the distal end of a lead connected to an implantable stimulator, thereby allowing the electrode to be electrically connected with the implantable stimulator;

FIG. 16A illustrates compression of the metal bands around the ends of the silicone tube that insulates the connector of FIGS. 15A–15C;

FIG. 16B is a sectional view taken along the line 16B—16B of the connector of FIG. 15C;

FIG. 17C illustrates an insertion tool that may be used to insert the electrode assembly of FIG. 17A within the stapedius muscle tissue;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 17A:
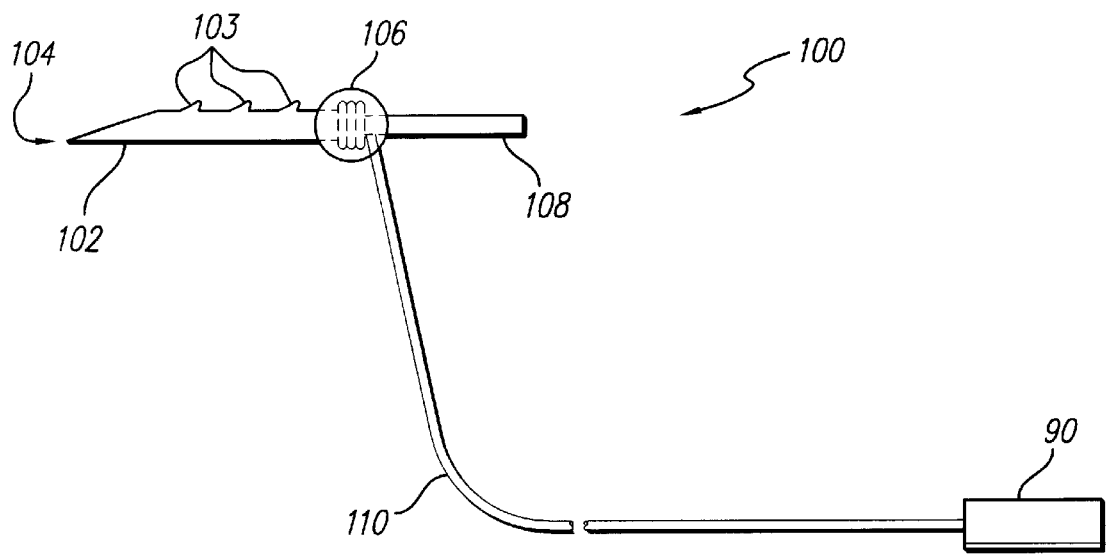
FIG. 17A depicts a first preferred embodiment of a stapedius electrode assembly made in accordance with the present invention.
Figure 17B:
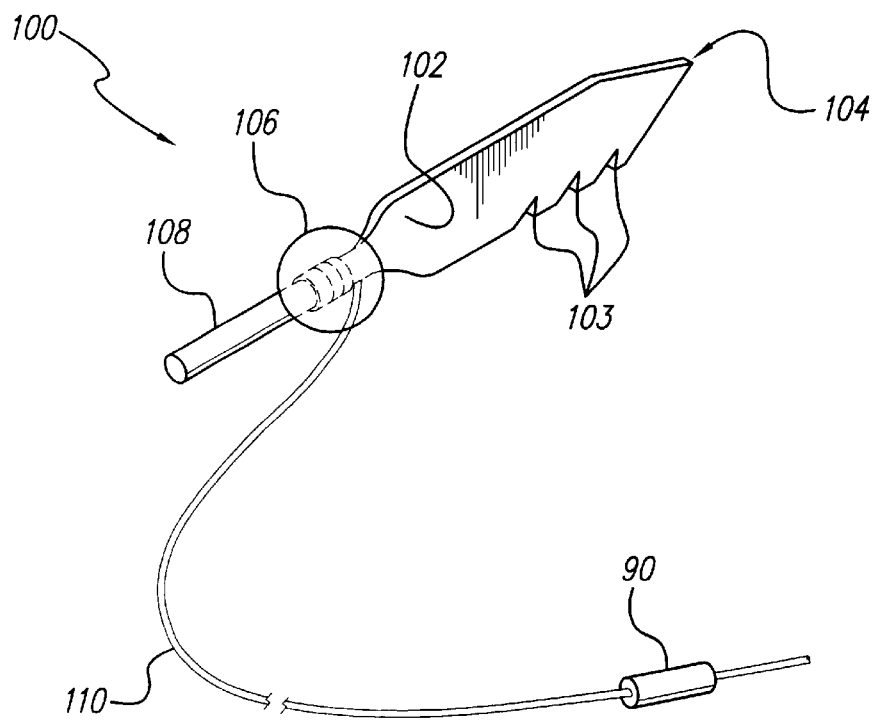
FIG. 17B is a perspective view of the electrode assembly of FIG. 17A.

A first preferred embodiment of an electrode assembly 100 used for sensing the stapedius reflex is shown in FIGS. 17A and 17B. The electrode assembly 100 includes a relatively flat blade 102, having a sharp point 104 at its distal tip. A plurality of serrations 103 are preferably formed along one edge of the blade 102. A proximal end 108 of the electrode assembly 100 is a round shank or rod, having a diameter of approximately 0.1 mm. The electrode assembly is typically formed by starting with solid Pt wire having a diameter of approximately 0.1 mm and flattening the distal end to form the flat blade 102. When formed, the flat blade 102 has a thickness of about 0.05 mm. The serrations 103 and the sharp distal point 104 are then formed in the flattened blade portion, e.g., by trimming with a steel blade or special trimming tool. When completed, the overall length of the electrode assembly 100 is about 2 mm, with the flat blade 102 being at least about 1.0 mm in length.

Still referring to FIGS. 17A and 17B, a suitable wire 110, e.g., a flexible Teflon-coated Pt/Ir wife having a diameter of about 25 microns (where a micron=0.001 mm), is mechanically and electrically attached to the electrode assembly near the point where the flat blade 102 flares out to the round proximal end portion 108. This wire 110 may be formed to be coiled or straight. The wire is welded to the round shank to make a good electrical contact. Typically, this welding is done through the insulation, but if necessary, the insulation may be stripped. The wire is also wrapped 2 to 3 times around the shank 108 to form a mechanical strain relief. These two or three turns of the wire 110 not only assure a good electrical connection between the blade electrode 102 and the wire 110, but also provide a good mechanical connection therebetween. A blob 106 of epoxy, having a diameter of about 0.3 mm, may be placed over the wire turns in order to protect the weld, and to keep the turns from unwinding, and to thus maintain a good electrical and mechanical connection. A suitable connector 90, described more fully below in conjunction with FIGS. 15A–15C, may then be attached to a proximal end of the wire 110 in order to allow the wire 110 to be detachably connected to appropriate electrical circuitry used to monitor the electrode 100 for a stapedius reflex.

In order to insert the electrode assembly within the middle ear so that it is maintained in contact with the stapedius muscle tissue, an insertion tool 120, of the type illustrated in FIG. 17C, may be employed. The tool 120 has an overall length that allows it to be conveniently held within the hand of the surgeon, or other medical personnel, who is performing the implant operation. A handle 122 is provided at a proximal end of the tool 120 to which a barrel 124 is attached. The barrel 124 extends out to a distal end piece 126 that includes a hollowed tip in which the round end 108 of the electrode assembly 100 may be received. Before inserting the electrode assembly 100 in the hollowed tip of the distal end piece 126 of the tool 120, the electrode assembly 100 is threaded through a collar 128. The collar 128 is preferably made from a biocompatible silastic material. The collar 128, with wire 110 passing therethrough, is slid over the barrel 124 of the tool 120. With the electrode assembly 100 inserted into in the tip 126 of the tool 120, and with the collar 128 slid onto the barrel 124 of the tool 120, and with the wire 110 passing through the collar 128, the insertion tool 120 is fully loaded and ready to be used to implant the electrode assembly 100 in the stapedius reflex muscle tissue.

Figure 18A:
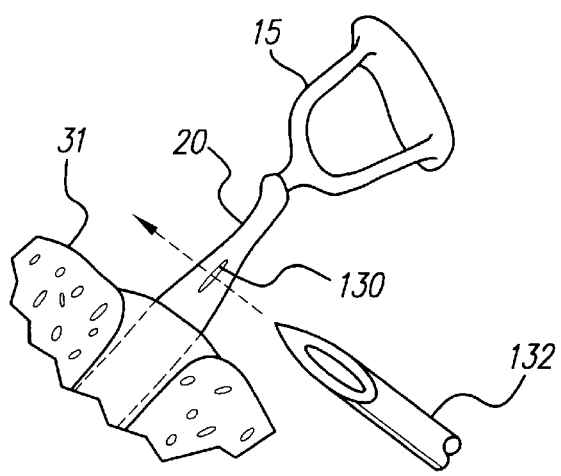
FIGS. 18A–18E illustrate the sequence of steps used to implant the stapedius electrode assembly of FIG. 17A into the stapedius muscle.

A preferred manner of implanting the electrode assembly is depicted in FIGS. 18A through 18E. As seen in FIG. 18A, a first step is to make a small slot or slit 130 in the exposed stapedius muscle tissue 20 or in the tendon that is attached to the stapes 15. This may be done using any small, sharp pointed instrument, such as a 30 gauge (G) needle 132. The stapedius muscle 20 connects to the stapes 15 through a bony channel 30 formed in bone tissue 31 (see, e.g., FIG. 2).

Figure 18B:
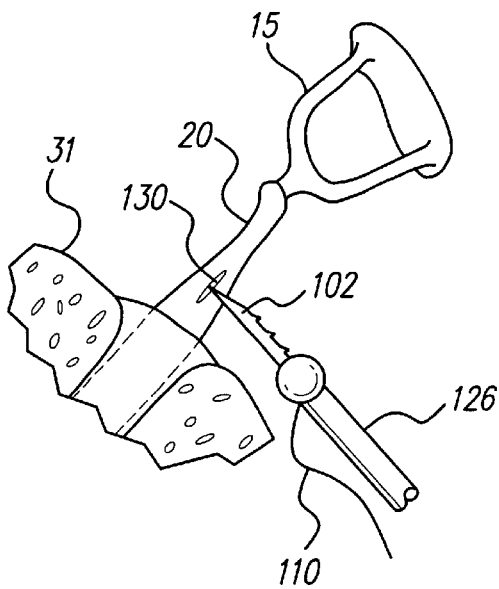
Figure 18C:
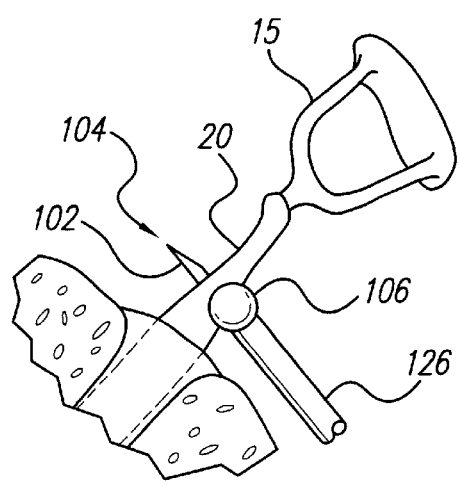

As a next step, shown in FIG. 18B, the tip 104 of the blade electrode 102 is positioned at the slot 130. Then, as illustrated in FIG. 18C, the electrode is pushed into the slot 130 using the tool 120. During this insertion process, the epoxy blob 106, located near the midpoint of the electrode assembly 100, functions as a stop which defines the maximum insertion depth of the blade electrode 102. Hence, when fully inserted into the stapedius muscle 20, the blob 106 of the electrode assembly 100 rests firmly against the muscle tissue 20. Moreover, the serrations 103, formed along one edge of the blade electrode 102, are slanted in a direction that makes it difficult for the blade electrode 102 to move backwards out of the slot 130. Thus, when fully inserted into the muscle tissue 20, the blade electrode 102 is firmly held in position within the slot 130 by the serrations 103 on one side of the tissue and the blob 106 on the other side of the tissue.

Figure 18D:
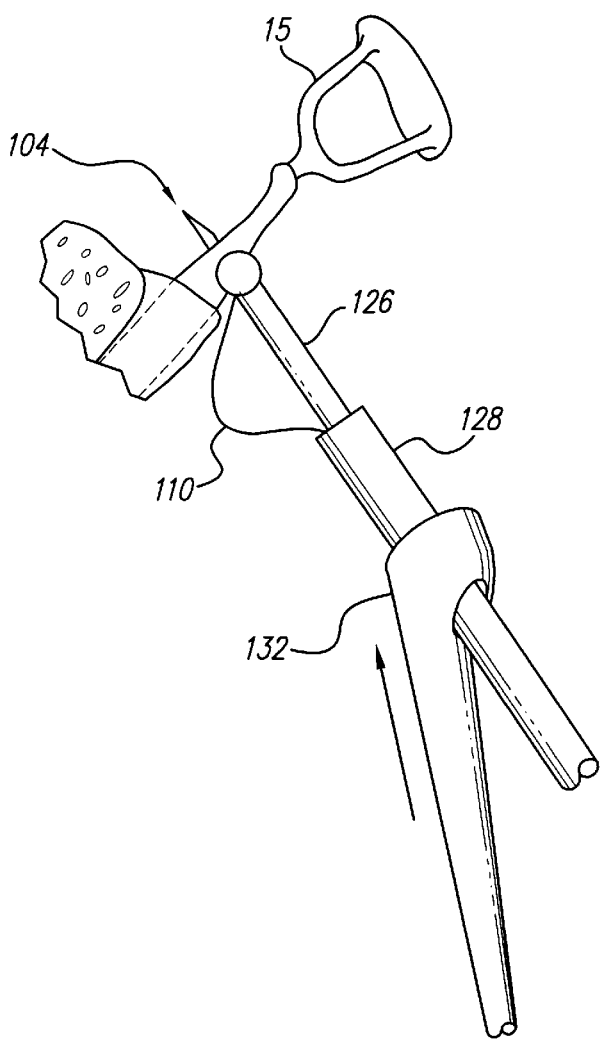
Figure 18E:
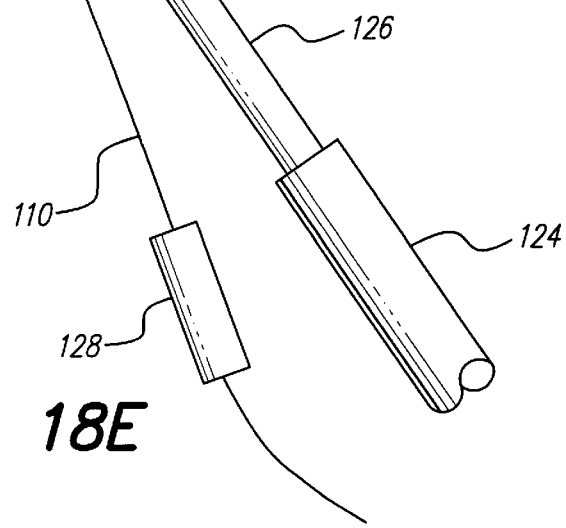

In order to remove the tool 120, the collar 128 is pushed forward off of the barrel 124, and along the distal end piece 126, using a suitable cochlear claw 132, or equivalent instrument, as illustrated in FIG. 18D. As the collar is pushed all the way to the distal end of the tool, it engages the blob 106 and applies a reverse force on the tool that causes the hollowed distal tip portion of the tool 120 to pull out of the rounded portion 108 of the electrode assembly 100, as shown in FIG. 18E, thereby disengaging the tool 120 from the electrode assembly 100. The tool 120 may then be removed, leaving the collar 128 around the wire 110. The collar 128 may remain implanted in the middle ear along with the electrode assembly 100.

Figure 19A:
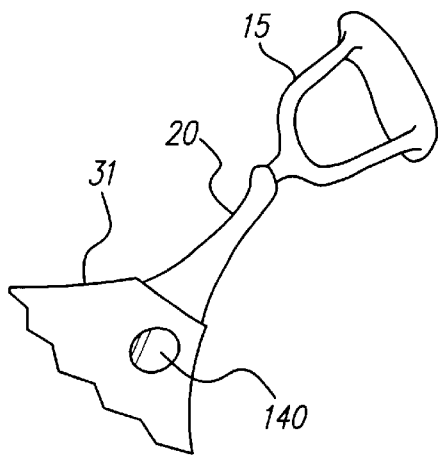
FIGS. 19A–19D illustrate the sequence of steps used to implant the stapedius electrode assembly of FIG. 17A, or an electrode assembly similar thereto, so as to position a side surface area of the electrode to lie against the stapedius muscle within the bony channel.
Figure 19B:
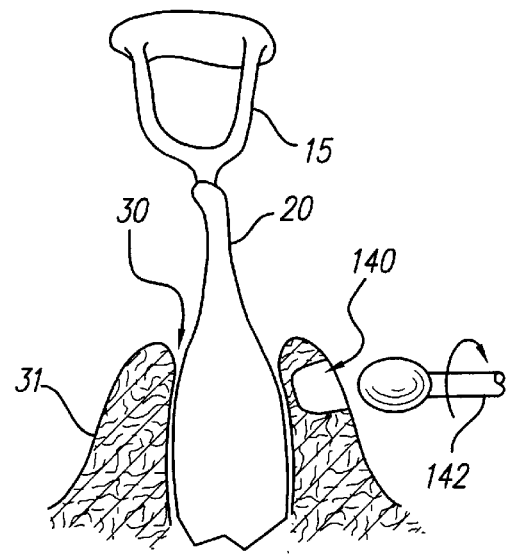

Turning next to FIGS. 19A through 19D, a second preferred manner of implanting the stapedius reflex electrode assembly 100, or equivalent electrode assembly, within the stapedius reflex muscle 20 is illustrated. FIGS. 19A and 19B depict the stapes 15 attached to the stapedius reflex muscle tissue 20. As seen best in the side view of FIG. 19B, the muscle tissue 20 resides in a bony channel 30 within bone structure 31. The preferred attachment method calls for making an opening 140 in the bony structure 31 so as to expose the muscle tissue 20 within the bony channel 30. Such opening or hole 140 may be made using any Suitable instrument, such as a surgeon's drill 142.

Figure 19C:
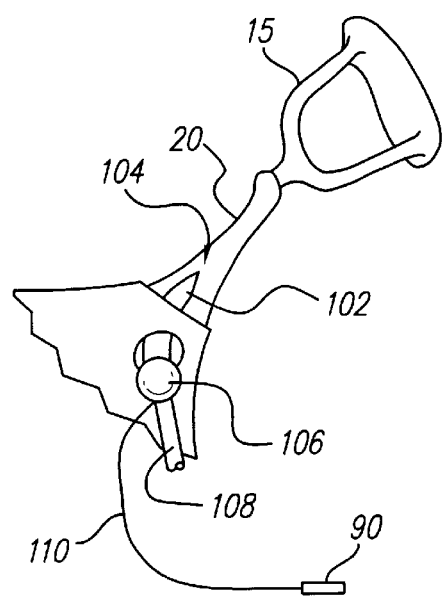
Figure 19D:
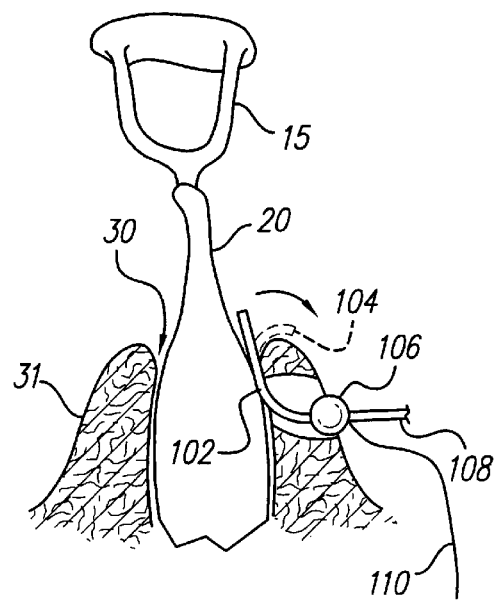

Once the opening 140 has been made, the tip 104 of the electrode assembly 100 is inserted through the opening and up through the bony channel 31, so as to protrude from the bony channel, as seen in FIGS. 19C and 19D. That portion of the electrode tip 104 that protrudes out of the bony channel 30 is then bent over, as seen in FIG. 19D, so as to fit snugly against the bone structure 31. Advantageously, the entire side of the electrode 102 lies against the stapedius muscle tissue 20, thereby providing a relatively large surface area over which stapedius reflex muscle activity may be sensed.

It should be noted that the electrode assembly used with the implant method shown in FIGS. 19A through 19D need not be identically the same as the electrode assembly 100 shown, e.g, in FIGS. 17A and 17B. For example, serrations 103 along one edge of the electrode blade may not be required, although serrations may be used if desired. Numerous types of elongate electrodes may be used with the technique shown in FIGS. 19A through 19B, including round electrodes, flat electrodes, multi-filar electrodes (see, e.g., FIG. 13), and the like.

Figure 1:
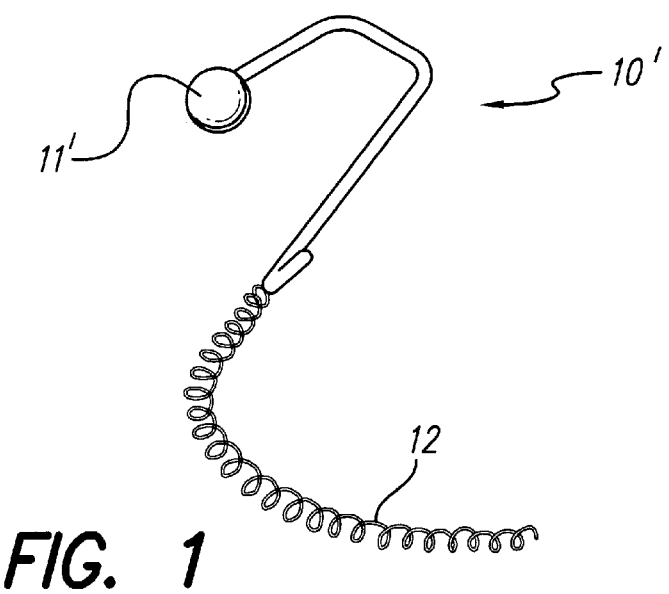
FIG. 1 illustrates a first alternative embodiment of a stapedius electrode made in accordance with the present invention.

Next, turning to FIG. 1, a first alternative embodiment of a stapedius reflex electrode 10' made in accordance with the present invention is shown. The electrode is made from a biocompatible metal wire, preferably iridium, which is shaped into a hook with a small ball 11' at one end. The other end is connected to a light, coiled, insulated lead 12 that provides a connection to the implant circuitry (not shown). The hook 10' is preferably insulated, except for the surface of the ball.

Figure 2:
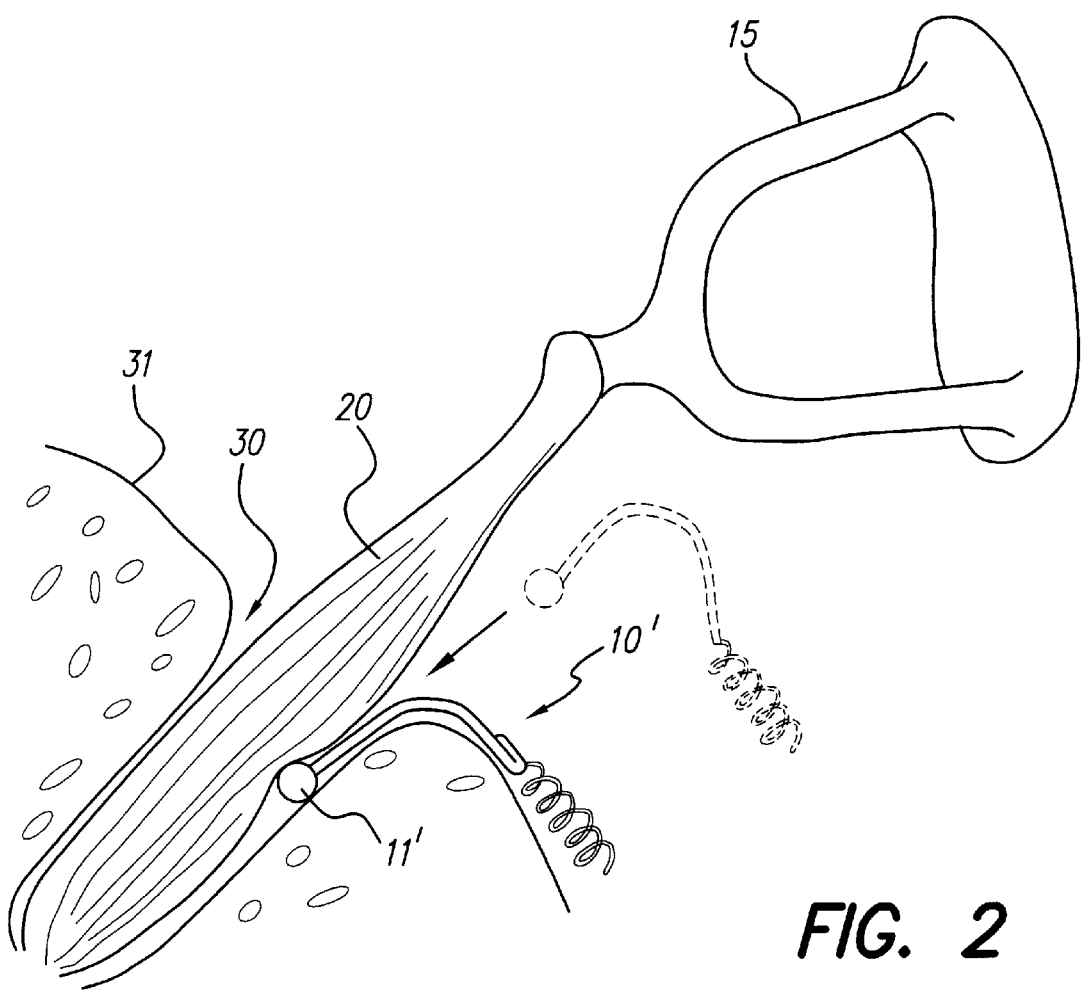
FIG. 2 illustrates how the electrode of FIG. 1 is positioned during implant surgery.

During implant surgery, the ball 11' is pressed against the stapedius muscle 20 into the bony channel 30, near the stapes 15, as illustrated in FIG. 2. The ball 11' should be partially embedded in the surface of the muscle 20. thereby providing good electrical contact and necessary stability. Advantageously, such partial embedding of the small ball into The stapedius muscle at the bony channel 30 does not create undue trauma or stress for the muscle.

Figure 3:
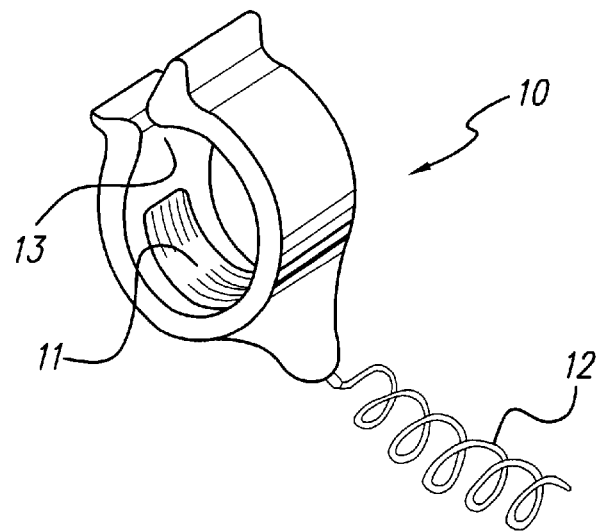
FIG. 3 shows a second alternative embodiment of a stapedius electrode.

A second alternative embodiment of a stapedius reflex electrode 10 is shown in FIG. 3. As seen in FIG. 3, such electrode 10 includes an electrical contact 11, made from a biocompatible metal foil, embedded within a silicone mold 13. The metal foil may be, e.g., platinum, iridium, stainless steel, or the like. The silicone mold 13 is shaped into a cuff configuration, with an opening slightly smaller than the diameter of the end of the stapedius muscle 20 extending out of bone channel 30.

Figure 4:
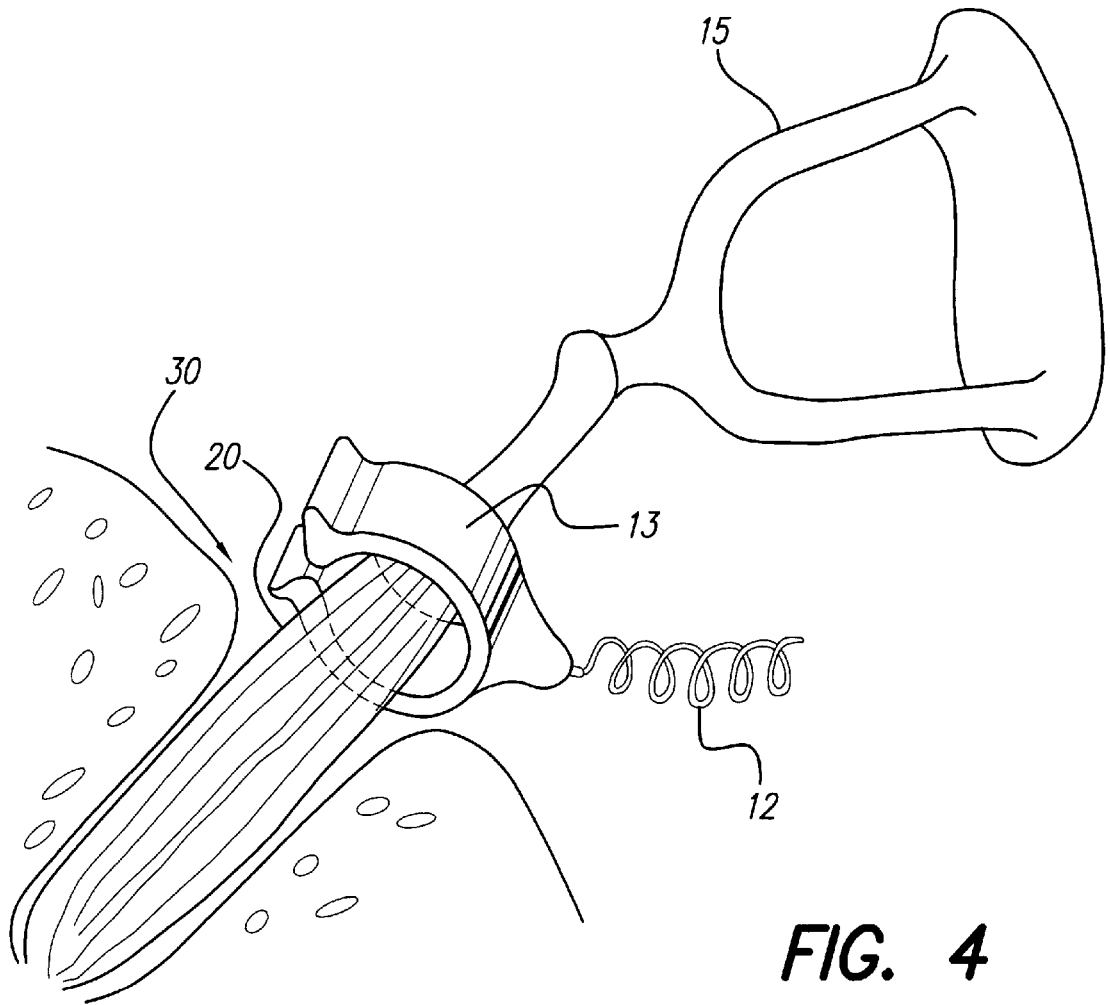
FIG. 4 depicts how the electrode of FIG. 3 is positioned relative to the stapedius muscle during implant surgery.

The silicone cuff has an opening allowing easy assembly of the electrode by clipping the cuff over the exposed muscle, near the stapes 15, as shown in FIG. 4. Electrical connection of the electrode 10 to the implant circuitry is provided by a flexible coiled, insulated lead 12.

Advantageously, by using a cuff that encircles The stapedius muscle 20, very little trauma or stress is created for the muscle, and The stapedius reflex within the muscle may be accurately and safely monitored.

Figure 5:
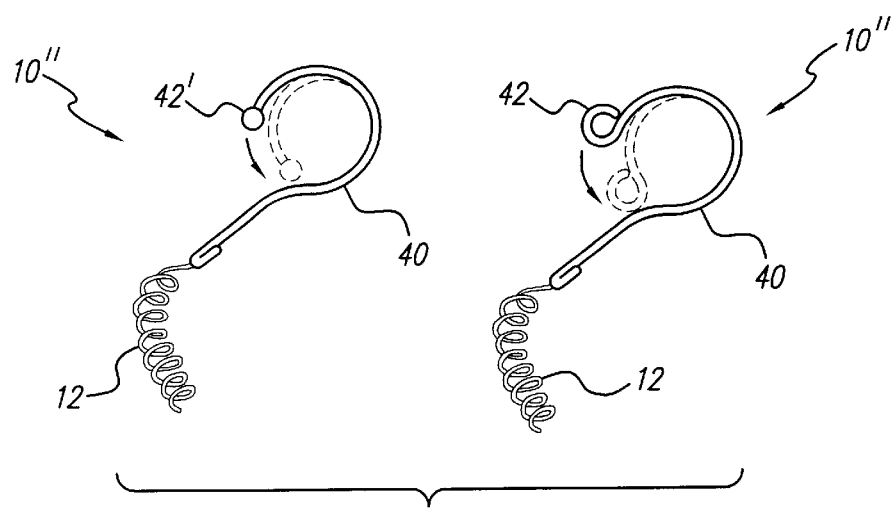
FIG. 5 illustrates a third alternative embodiment of a stapedius muscle electrode.

Turning next to FIG. 5, a third alternative embodiment of a stapedius muscle electrode 10" is illustrated. The electrode 10" includes an electrode made from soft, annealed, platinum wire 40 formed into a hook shape. One end is formed into a loop 42 (shown on the right side of FIG. 5), or ball 42' (shown on the left side of FIG. 5). The other end is connected to a coiled, insulated lead 12. The electrode 10" is placed over the visible end of the stapedius muscle 20 and crimped over the muscle to stabilize it and to provide direct contact with the muscle. By surrounding The stapedius muscle, as described, very little trauma or stress is created for the muscle, yet a reliable, safe detection of the muscle reflex may be monitored.

Figure 6:
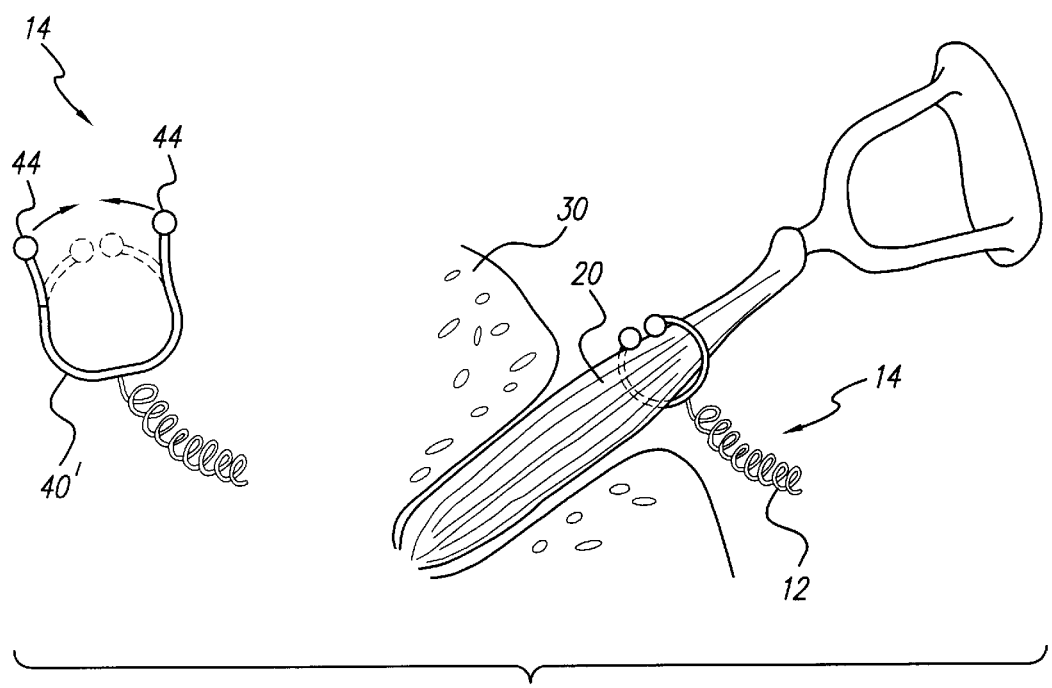
FIG. 6 shows a fourth alternative embodiment of a stapedius muscle electrode.

A fourth alternative embodiment of a stapedius muscle electrode 14 is made from soft, annealed, platinum wire 40' formed into a U shape, as shown in FIG. 6. The ends of the electrode 14 are looped, or flamed into a ball 44. A flexible, coiled, insulated lead 12 is connected preferably in the middle of the U-shaped wire 40'. The electrode is placed over the stapedius muscle 20 and crimped to provide stability and contact.

Advantageously, by crimping the U-shaped electrode 14 around The stapedius muscle, with loops or balls at the ends, very little damage, if any, is done to the muscle tissue, and a safe and reliable muscle reflex may be detected.

Turning next to FIG. 7, a fifth alternative embodiment of a stapedius muscle electrode 16 is illustrated. As seen in FIG. 7, the electrode 16 is formed from multistrand platinum/iridium (Pt/Ir) wire 50. (there, and elsewhere throughout this application, Pt/Ir is an exemplary material, and is not intended to be limiting. The wire 50 may be made from other biocompatible materials, as well.) As depicted in the top portion of FIG. 7, a distal end 51 of the wire 50 is flamed to form a ball 52. The ball 52 has a diameter of between about 0.3 mm and 0.5 mm, e.g., approximately 0.4 mm. The wire 50 may or may not be insulated, e.g., with Teflon insulation. If insulated, then the insulation may be removed from the distal end prior to flaming to form the ball 52, or the insulation may simply to burned off as the ball 52 is formed.

FIGS. 8A and 8B show a preferred implant tool 60 that may be used to implant a ball electrode 16 of the type shown in FIG. 7. The implant tool 60 includes a handle 62 from which a shank portion 64 extends. The shank 64 is bent in a hook shape near its distal tip 66. As seen best in FIG. 8B and the sectional view of FIG. 8C, the shank 64 is preferably formed in a U-shape so as to create an open channel or groove 67 that passes therethrough. The hook formed at the distal tip 67, as seen in FIG. 8B, has a cut made in the U-shaped channel material such that an angle a of less than 90 degrees is formed. This cut angle α, as seen from the explanation presented below, helps hold the ball electrode 52 in place within the tool 60 during the implant process.

Figure 9:
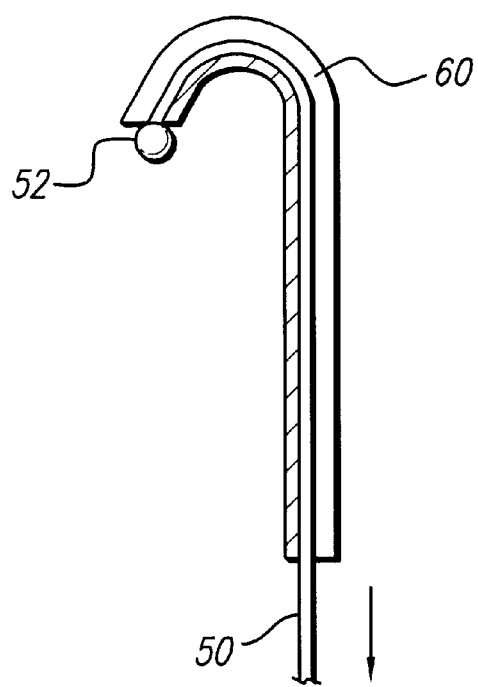
FIG. 9 illustrates the manner in which the ball electrode of FIG. 7 is mounted on the tool of FIGS. 8A–8C.
Figure 10:
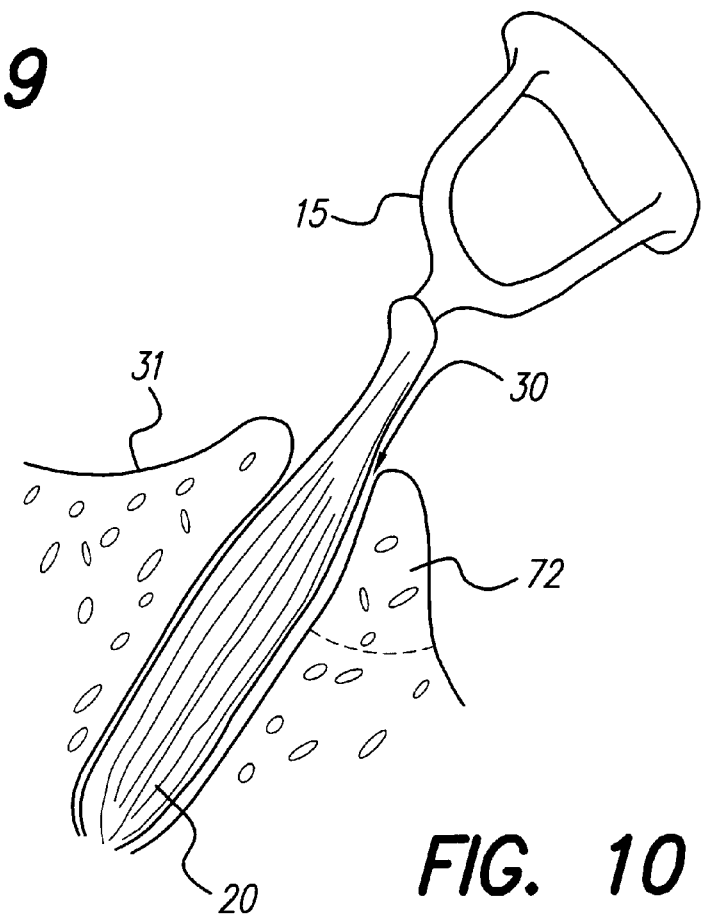
FIG. 10 diagrammatically illustrates removal of the bony wall near the stapedius muscle in order to implant the ball electrode of FIG. 7.
Figure 11:
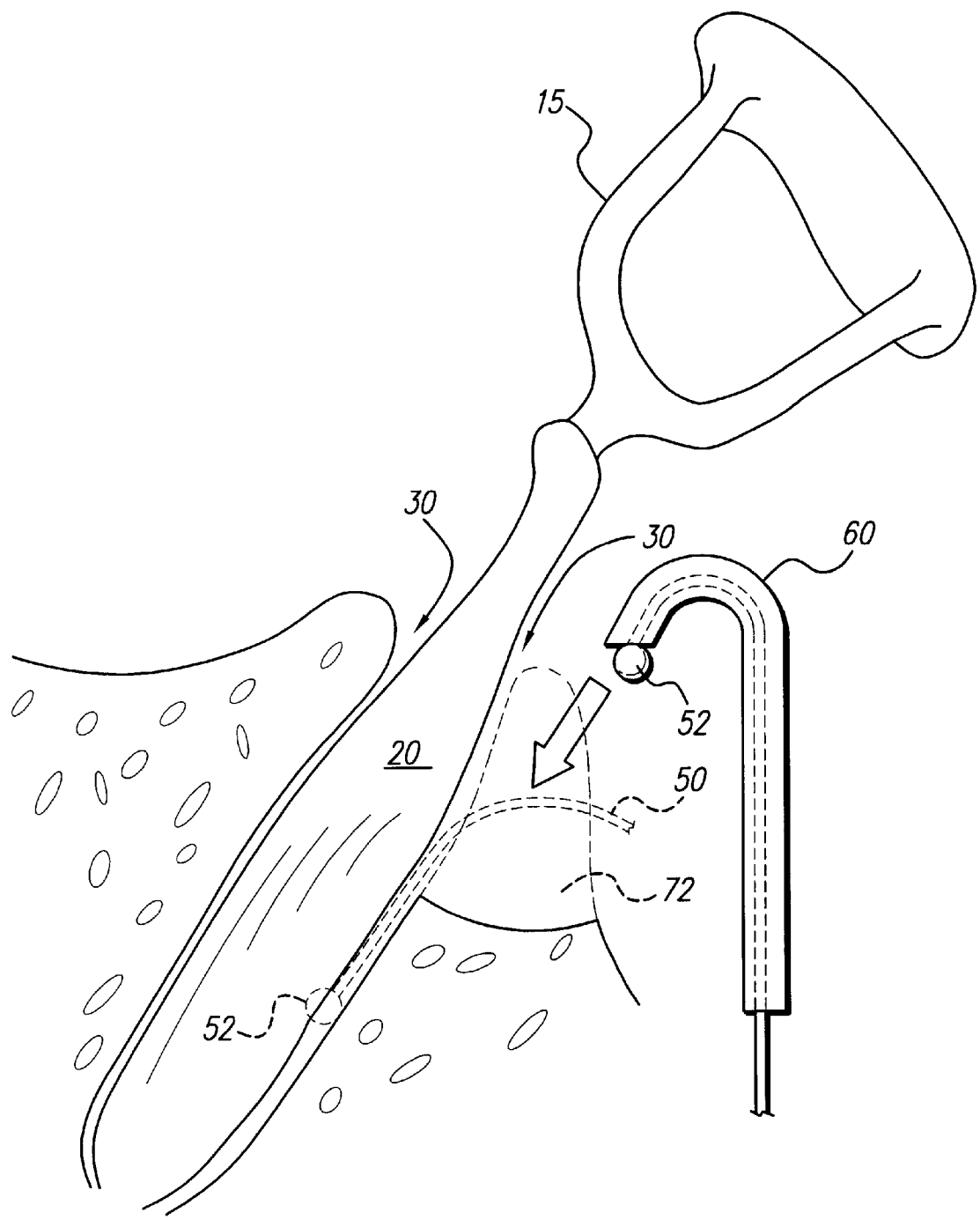
FIG. 11 illustrates implantation of the ball electrode shown in FIG. 7 into the space between the stapedius muscle and bony wall using the implant tool shown in FIGS. 8A–8C.

Turning next to FIGS. 9, 10 and 11, the manner of using the tool 60 to implant the ball electrode 16 is illustrated. As seen in FIG. 9, the ball 52 at the distal end of the ball electrode 16 is first placed at the distal tip 66 of the implant tool 60. The lead wire 50 is placed in the groove 67 and stretched by applying a tension force on the proximal end of the wire. This applied tension holds the ball electrode 16 securely at the distal tip 66 of the tool 60, allowing easy maneuverability and placement of the electrode once the implant process begins.

The implant process is illustrated in FIGS. 10 and 11. As seen in FIG. 10, a small section 72 of bone around the bony channel 30 through which the stapedius muscle 20 passes is removed. This section 72 of bone may be removed by drilling or chipping. Next, as shown best in FIG. 11, the distal tip 66 of the implant tool 60, with the ball 52 of the ball electrode 16 held therein, is inserted into the bony channel 30 through the access created by the removed bone to a depth determined by the amount of shank which is hooked at the distal end of the tool 60. The ball 52 is thus lodged between the bone and the muscle 20. The tension on the lead wire 50 is then released, and the tool 60 is withdrawn, leaving the ball electrode 52 in a stable position, squeezed between the stapedius muscle 20 and the bony wall. Advantageously, after a few weeks without stimulation, the ball electrode 52 will partially erode the bone at the pressure point, thereby creating or forming a small socket or recess in which the ball electrode 52 is held in a stable position.

Figure 12A:
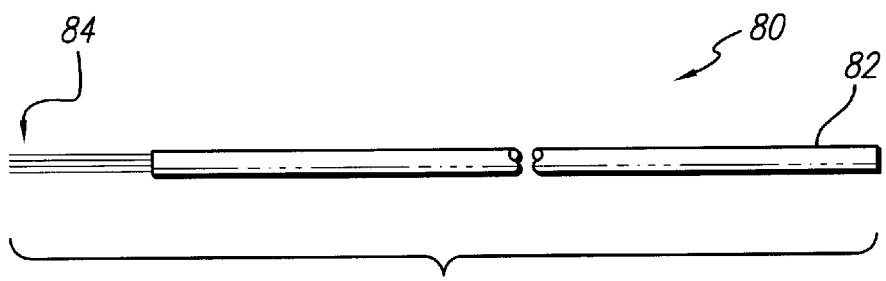
FIGS. 12A, 12B and 12C illustrate a sixth alternative embodiment of a stapedius harpoon electrode made by stripping insulation from a distal end of Teflon coated multistrand wire (FIG. 12A), loading the wire in a delivery needle (FIG. 12B), and folding the stripped wires backwards on the needle (FIG. 12C)
Figure 12B:
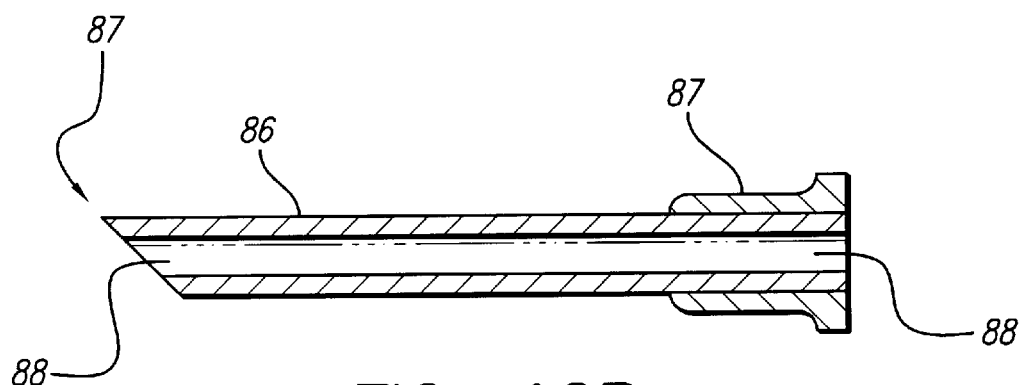
Figure 12C:
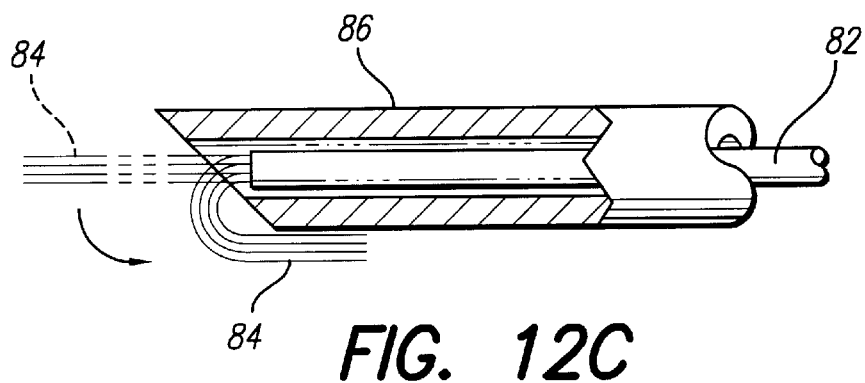

Next, turning to FIGS. 12A, 12B and 12C, a sixth alternative embodiment of the invention is illustrated. This sixth alternative embodiment has been referred to as a stapedius harpoon electrode 80. The harpoon electrode 80 is made, as seen in FIG. 12A, by first stripping about 0.5 to 1.5 mm of insulation from a distal end 84 of Teflon coated multistrand Pt/Ir wire 82, e.g., by flaming. Then, the wire 82 is loaded in a delivery needle 86, as shown in FIG. 12B. The delivery needle 86 is attached to a handle 87, and has an outer diameter of approximately 0.4 mm. A lumen 88 passes longitudinally through its center. The needle 86 includes a sharp tip 87 to facilitate its penetration into body tissue. The lumen 88 has a diameter such that the wire 82, with insulation thereon, may be readily passed therethrough. The wire 82 is pushed through the lumen 88 until the distal portion 84, without insulation, protrudes from the tip of the needle. This electrode portion 84 of the harpoon electrode 80 is then bent backwards over of the outside body of the needle 86 a distance of about 0.5 to 1.0 mm, as seen in FIG. 12C.

Figure 13:
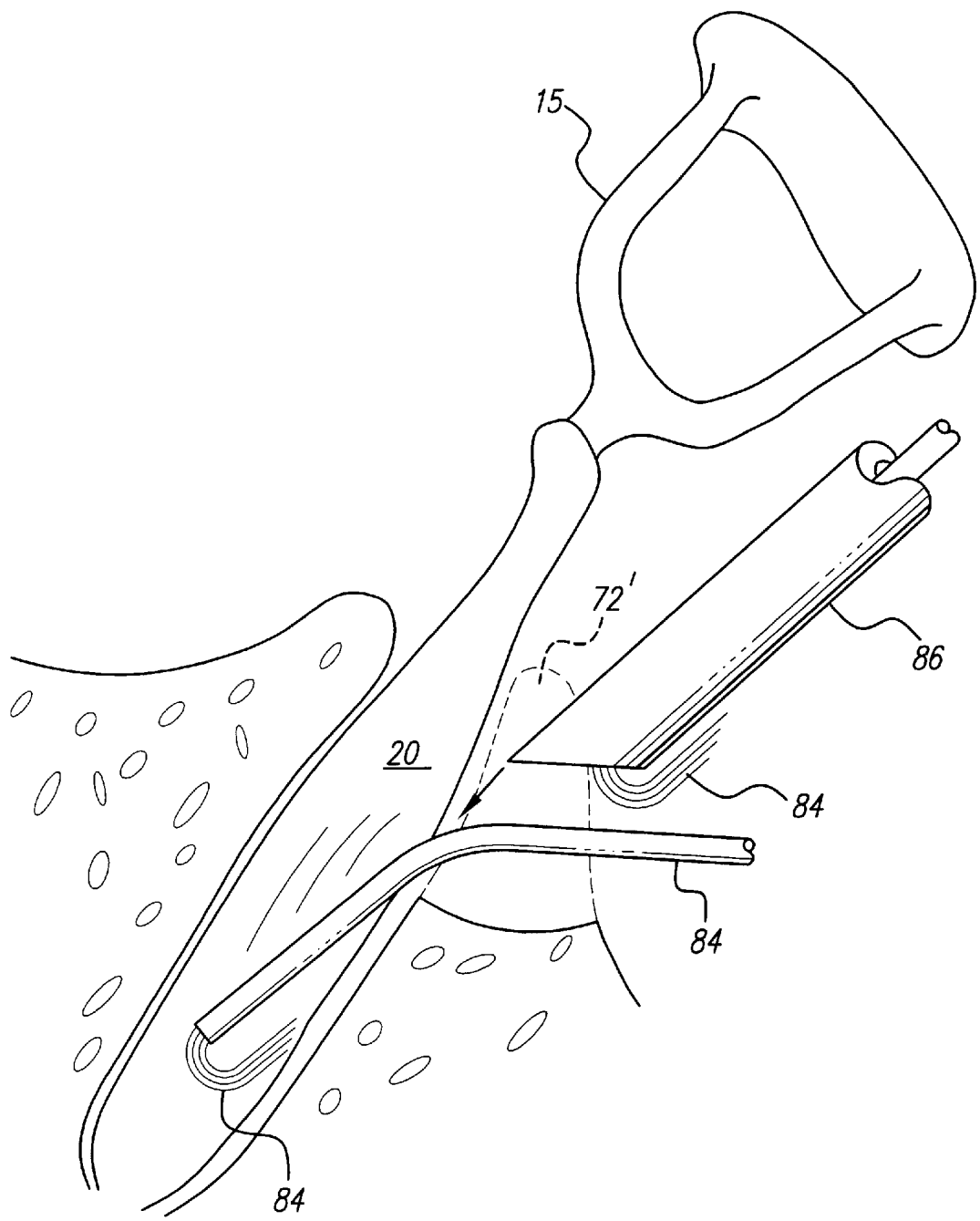
FIG. 13 diagrammatically illustrates one manner of implantation of the harpoon electrode of FIGS. 12A–12C into the stapedius muscle through an opening formed in the bony wall.
Figure 14:
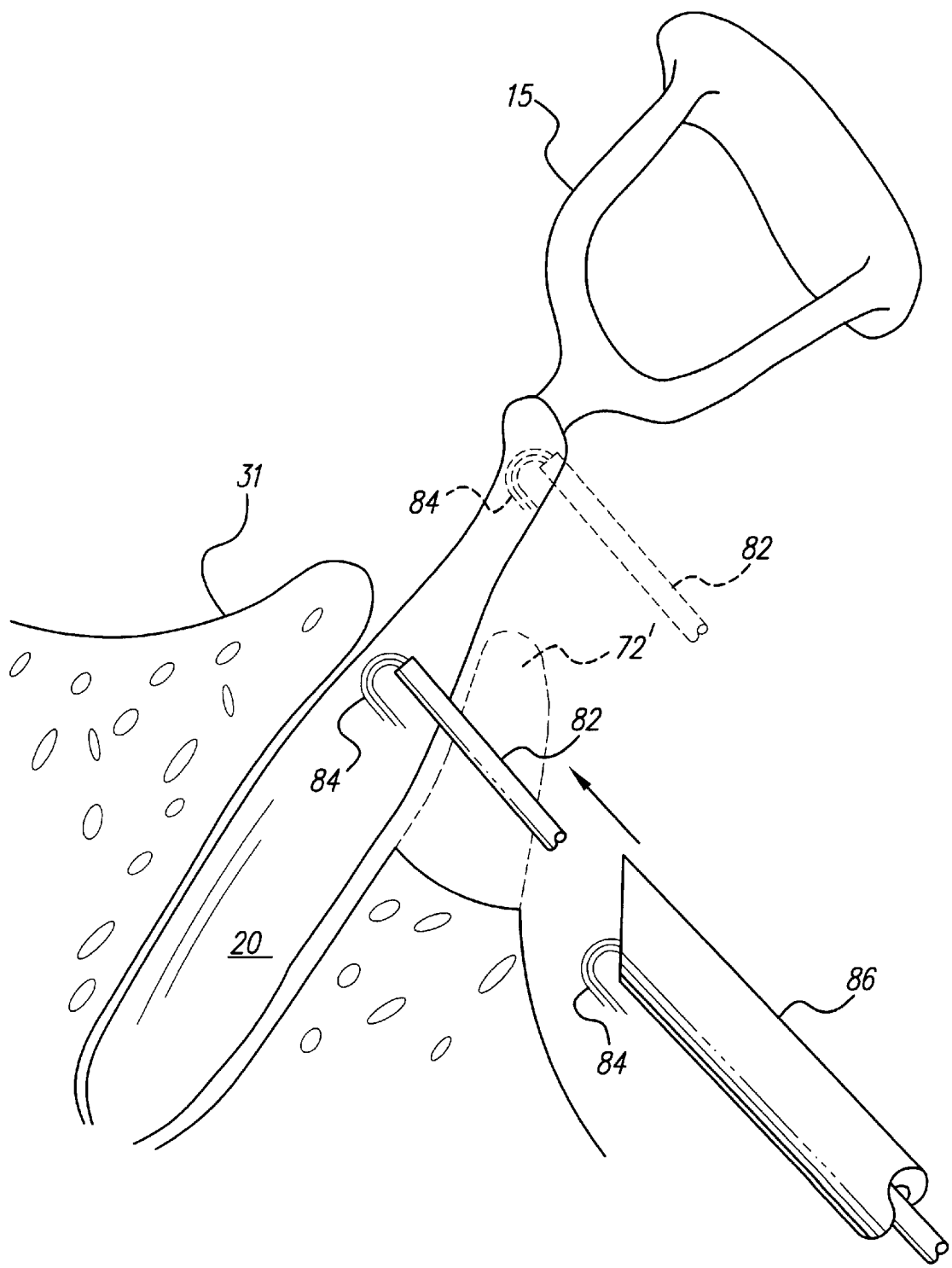
FIG. 14 diagrammatically illustrates another manner of implantation of the harpoon electrode of FIGS. 12A–12C into the stapedius muscle through an opening formed in the bony wall, or in the tendon between the bony channel and the stapes.

In order to implant the harpoon electrode 80, a small hole (large enough for the needle 86 to pass therethrough) is drilled in the bony wall surrounding the stapedius muscle 20. Alternatively, part of the bony wall 72' may be removed from the region around the stapedius muscle by drilling or chipping away. A second way to implant the electrode is to place the electrode into the tendon of the muscle between the bony channel and the stapes. Then, as seen in FIG. 13 or FIG. 14, the tip of the delivery needle 86 is pushed through the opening (or removed bone portion 72') into the stapedius muscle 20, forcing the folded-back electrode tip 84 to become embedded in the tissue of the stapedius muscle 20. The folded-back end 84 of the electrode lead 82 is grabbed by the surrounding tissue, allowing removal of the delivery needle 86 and leaving the tip 84 of the electrode harpoon 80 securely fixed in the muscle. FIG. 13 diagrammatically illustrates one manner of implantation of the harpoon electrode 80 into the stapedius muscle 20 through an opening formed in the bony wall; and FIG. 14 diagrammatically illustrates another manner of implantation of the harpoon electrode 80 into the stapedius muscle 20 through an opening formed in the bony wall.

Insertion (implantation) of either the stapedius ball electrode 16, the stapedius harpoon electrode 80, or any of the other electrodes described herein, see, e.g., the electrode illustrated in FIGS. 17A through 19D, may be made easier if the electrode is not attached to the implantable simulator at the time of implant operation. This is not to suggest that such stapedius electrodes could not be implanted while attached to the implant device, because generally they could; rather, it is just that the implant operation is generally made easier if the connection to the implant device is not yet made. Thus, there remains a need for a connector that electrically connects the implanted stapedius electrode with the implant device. Such a connector is described next in connection with FIGS. 15A, 15B, 15C, 16A and 16B. The construction of a preferred tube connector 90 is illustrated in FIGS. 15A–15C, and its use is illustrated in FIGS. 16A–16B.

In FIGS. 15A–15C and 16A–16B, it is assumed that the stapedius electrode that has been implanted in the harpoon electrode 80 of the type illustrated in FIGS. 12A–12C and FIGS. 13 and 14. However, such is only exemplary, and it is to be understood that the connector herein described could be used with any type of electrode.

As seen in FIG. 15A, a preferred tube connector 90 that may be used to attach the proximal end 83 of a harpoon electrode 80 to a wire 91 coming from an implant device (not shown) includes a small section of platinum tubing 92, one end of which is crimped over or welded to the distal end of the wire 91. On the lead 91 there is also placed a section of silicone tubing or sleeving 94. The silicone tube or sleeve 94 has an internal diameter that allows it to freely slide over the platinum tubing 92. The silicone tube or sleeve 94 further has a platinum band 96 placed on each end.

Once the stapedius electrode has been lodged (implanted) in a desired location, the lead wire 82 from the electrode is cut to the desired length (FIG. 15A). Then, as shown in FIG. 15B, the proximal end 83 of the lead wire 82 is placed within the opening of the tube 92, and the tube end is then squeezed or crimped with forceps (or another suitable tool) to cut through the Teflon insulation of the lead wire 82. This assures that good electrical contact is made between the tube and the multistrand wires included within the lead wire 82. Then, as seen in FIG. 15C, the silicone tube or sleeve 96 is slid over the platinum tube 92, and both of the platinum bands 96 are squashed, using a suitable tool 97, as seen in FIG. 16A. The result is that the openings of both ends of the silicone tube 94 are closed, as seen in the sectional view of FIG. 16B, thereby insulating the connector 90 from body tissue and fluids.

While platinum is a preferred material for the tube 92 and bands 96, it is to be understood that other biocompatible materials may also be used, such as iridium, stainless steel, or alloys thereof. The only restraint, other than biocompatibility, is that the tube 90 be electrically conductive. The bands 96 need not be electrically conductive, but should be a material that when crimped, or tied, is able to maintain closure of the ends of the silicone tube 96.

As described above, it is thus seen that the present invention advantageously provides a stapedius muscle electrode that may be used within the middle ear in direct contact with the stapedius muscle, thereby allowing the reflex of such muscle to be monitored.

As further described above, it is also seen that the invention provides a stapedius muscle electrode which allows effective signal detection to occur without damaging the integrity of the stapedius muscle.

Moreover, it is seen that the invention described herein provides a stapedius muscle electrode that is inexpensive to manufacture, easy to implant, and which can be readily connected to an implantable stimulator.

While the invention herein disclosed has been described by means of specific embodiments and applications thereof, numerous modifications and variations could be made thereto by those skilled in the art without departing from the scope of the invention set forth in the claims.

What is claimed is:

1. An electrode for attachment to the stapedius muscle tissue (20), which muscle tissue is visible as it exits a bony channel (30) of the middle ear of a human, comprising:
   a biocompatible metal wire formed into a specified shape;
   an insulated lead electrically and mechanically attached to the shaped metal wire;
   wherein the specified shape of the metal wire facilitates its implantation within the middle ear so as to secure its contact with stapedius muscle tissue.

2. The electrode as set forth in claim 1 wherein the specified shape comprises a flat blade at a distal end of the electrode and a round shank at a proximal end of the electrode, and wherein the flat blade has a sharp point at its distal end.

3. The electrode as set forth in claim 2 wherein the flat blade includes a plurality of serrations along one edge.

4. The electrode as set forth in claim 1 wherein the insulated lead is welded at a distal end to make electrical contact with the shaped metal wire, and wherein the lead is wrapped around the round shank a plurality of turns.

5. The electrode as set forth in claim 4 further including a blob of epoxy placed over the plurality of turns and shank to secure the turns to the shank.

6. The electrode as set forth in claim 5 wherein the biocompatible metal wire comprises a platinum wire having a diameter of approximately 0.1 mm.

7. A method of making a stapedius reflex electrode for use within the middle ear of a human comprising the steps of:
(a) flattening one end of the biocompatible wire to form a flat blade, the other end remaining as a round metal wire;
(b) electrically and mechanically attaching an insulated lead to the electrode near the point where the electrode transitions from the flat blade to the round wire;
(c) covering the point where the lead attaches to the electrode with a blob of epoxy; and
(d) forming a sharp tip at the end of the flat blade.

8. The method of claim 7 further including forming a plurality serrations along at least one edge of the flat blade, the serrations being formed with a slant that facilitates movement of the blade through muscle tissue in a forward direction and inhibits movement of the blade through the muscle tissue in a backwards direction.

9. A method of inserting a stapedius electrode within the stapedius muscle of a human, the stapedius muscle tissue being visible within the middle ear as it exits a bony channel prior to attaching to the stapes, the stapedius electrode having a flat blade with a sharp point on one end, a round wire on the other end, and further having an electrical lead attached thereto, the method comprising the steps of:
(a) forming a slot in the stapedius muscle tissue near the point where it is visible as it exits the bony channel;
(b) holding the electrode by its round end and inserting the sharp point of the flat blade through the slot; and
(c) securing the electrode within the slot.

10. The method of claim 9 wherein step (c) comprises forming serrations along one edge of the flat blade that facilitate movement of the blade through muscle tissue in a forward direction and inhibit movement of the blade through muscle tissue in a reverse direction, forming a stop on the electrode near the point where the flat blade transitions to the round wire, inserting the electrode through the slot in the forward direction until the stop engages the muscle tissue; whereby the electrode is secured in the slot.

11. A method of inserting a stapedius electrode within the stapedius muscle of a human, the stapedius muscle tissue being visible within the middle ear as it exits a bony channel prior to attaching to the stapes, the stapedius electrode comprising an elongate metal electrode having an electrical lead attached thereto, the method comprising the steps of:
(a) forming an opening in the bone surrounding the bony channel so as to expose the muscle tissue;
(b) inserting a distal tip of the elongate metal electrode through the opening and through the bony channel in a direction towards the stapes along an inside edge of the bony channel until the distal tip of the elongate metal electrode protrudes from the body channel; and
(c) bending over the protruding distal tip of the electrode against an upper edge of the bone surrounding the bony channel.

12. An electrode for attachment to the stapedius muscle (20), which muscle is visible as it exits a bony channel (30), of the middle ear of a human, comprising:
a biocompatible metal wire formed into a hook (10');
a light, coiled, insulated lead (12) attached at one end of the hook;
a small ball (11) formed at the other end of the hook;
the hook being insulated;
the small ball not being insulated;
the small ball being adapted for partial embedding within the surface of the stapedius muscle at the point where the stapedius muscle exits the bony channel.

13. An electrode for attachment to the stapedius muscle (20), which muscle is visible as it exits a bony channel (30) within the middle ear of a human, comprising:
a silicone mold (13) shaped into a cuff configuration;
a biocompatible metal contact (11) embedded within the silicone mold;
a light, coiled, insulated lead (12) attached to the metal contact through the silicone mold;
the silicone mold having an opening allowing it to be opened and placed around The stapedius muscle.

14. The electrode of claim 13 wherein said biocompatible metal contact comprises a foil made from platinum, iridium, or stainless steel.

15. An electrode for attachment to The stapedius muscle (20), which muscle is visible as it exits a bony channel (30) of the middle ear of a human, comprising:
a biocompatible metal wire formed into a hook shape (10");
a light, coiled, insulated lead (12) attached at one end of the hook;
a small contact (42, 42') formed at the other end of the hook;
the hook being adapted for crimping around The stapedius muscle at the point where The stapedius muscle exits the bony channel.

16. The electrode of claim 15 wherein the small contact comprises a small ball (42).

17. The electrode of claim 15 wherein the small contact comprises a loop (42') formed in the wire.

18. An electrode for attachment to the stapedius muscle (20), which muscle is visible as it exits a bony channel (30) of the middle car of a human, comprising:
a biocompatible metal wire formed into a U shape (40');
a light, coiled, insulated lead (12) attached to the wire near the middle of the U;
a small ball (44) formed at each end of the U-shape;
the U-shaped being adapted for positioning around The stapedius muscle (20) at the point where The stapedius muscle exits the bony channel.

19. An electrode system adapted for attachment to muscle tissue within a bony channel comprising:
a ball electrode (52) formed at a distal end of a multistrand wire (50);
means for inserting the ball electrode between the muscle tissue and a wall of the bony channel.

20. The electrode system of claim 19 wherein the means for inserting the ball electrode between the muscle tissue and a wall of the bony channel comprises an insertion tool (60), the insertion tool having a handle (62) and a grooved shank (64), the grooved shank having a hook formed near its distal tip (66).

21. The electrode system of claim 20 wherein the distal tip (66) of the insertion tool (60) includes a cut angle (α) that is less than 90 degrees.

22. An electrode system adapted for attachment to stapedius muscle tissue within the middle ear of a human, comprising:

a harpoon electrode (80) formed from of a multistrand insulated wire (82) having a distal tip portion (84) from which insulation has been removed;

means for embedding the distal tip portion (84) of the harpoon electrode (80) into stapedius muscle tissue.

23. The electrode system of claim 22 wherein the means for embedding the distal tip portion (84) into stapedius muscle tissue comprises a delivery needle (86) into which the harpoon electrode (80) is loaded, the delivery needle having a lumen (88) therein through which the multistrand insulated wire (82) may slidably pass, the distal tip portion (84) being folded back against an outer surface of the delivery needle when the harpoon electrode is loaded therein.

24. The electrode system of claim 23 further including a tube connector (90) that connects a proximal end of the multistrand insulated wire (82) to a distal end of a wire (91) from an implant device, the connector (90) comprising:

a conductive tube having a first end electrically attached to the distal end of the wire (91);

the proximal end of the multistrand insulated wire being inserted into a second end of the conductive tube, the second end of the tube being crimped over the proximal end of the multistrand insulated wire so as to penetrate through insulation of the wire and make electrical contact with the multistrands of conductive wire carried therein; and a silicone tube placed over the conductive tube, the ends of the silicone tube being closed to prevent leakage of body tissue or fluids inside of the silicone tube.

25. The electrode system of claim 24 wherein the silicone tube includes a metal band around each end thereof, the metal band being deformed to maintain the ends of the silicone tube in a closed position.

26. The electrode system of claim 25 wherein the conductive tube and metal band are made from platinum, iridium, or stainless steel, or alloys of platinum, iridium or stainless steel.

27. An electrode system for sensing the stapedius reflex of a human comprising:

a stapedius electrode having an insulated multi-strand wire lead attached hereto, the stapedius electrode being implantable so as to contact stapedius muscle tissue;

a tube connector that connects a proximal end of the multi-strand insulated wire lead to a distal end of a wire from an implant device, the tube connector comprising:

a conductive tube having a first end electrically attached to the distal end of the wire;

the proximal end of the multi-strand insulated wire lead being inserted into a second end of the conductive tube, the second end of the tube being crimped over the proximal end of the multi-strand insulated wire lead so as to penetrate through insulation of the wire and make electrical contact with the multi-strands of conductive wire lead carried therein; and a silicone tube placed over the conductive tube, the ends of the silicone tube being closed to prevent leakage of body tissue or fluids inside of the silicone tube.

28. The electrode system of claim 27 wherein the silicone tube includes a metal band around each end thereof, the metal band being deformed to maintain the ends of the silicone tube in a closed position.

29. The electrode system of claim 28 wherein the conductive tube and metal band are made from platinum, iridium, or stainless steel, or alloys of platinum, iridium or stainless steel.

30. A method of sensing a stapedius reflex of a patient comprising:

forming an stapedius muscle electrode substantially as claimed in claims 1, 12, 13, 15, 18, or 19;

positioning the electrode so as to be in direct contact with the stapedius muscle; and connecting the lead of the electrode to appropriate sensing circuitry.

31. The method of claim 30 wherein the positioning step comprises lodging the electrode between the stapedius muscle and a bony wall.

32. The method of claim 30 wherein the positioning step comprises embedding a distal end of the electrode in stapedius muscle tissue at a location near where the stapedius muscle exits a bony channel.

33. The method of claim 30 wherein the embedding step comprises inserting the electrode through a lumen of a delivery needle, folding the distal tip of the electrode back against an outer surface of the needle, injecting the needle into stapedius muscle tissue, and removing the needle.

* * * * *